(12) United States Patent
Forsthovel et al.

(10) Patent No.: US 8,163,225 B2
(45) Date of Patent: Apr. 24, 2012

(54) METHOD AND APPARATUS FOR MANUFACTURING PLASTIC CONTAINERS WITH INFRARED ABSORPTION MONITORING

(75) Inventors: Jochen Forsthovel, Regensburg (DE); Rudolf Fiegler, Regensburg (DE); Ulrich Lappe, Regensburg (DE)

(73) Assignee: Krones AG, Neutraubling (DE)

( * ) Notice: Subject to any disclaimer, the term of this patent is extended or adjusted under 35 U.S.C. 154(b) by 75 days.

(21) Appl. No.: 12/425,600

(22) Filed: Apr. 17, 2009

(65) Prior Publication Data
US 2009/0261513 A1 Oct. 22, 2009

(30) Foreign Application Priority Data

Apr. 17, 2008 (DE) .......................... 10 2008 019 176
Aug. 22, 2008 (DE) .......................... 10 2008 039 375
Mar. 30, 2009 (EP) ...................................... 09156679

(51) Int. Cl.
*B29B 13/08* (2006.01)
(52) U.S. Cl. .................. 264/410; 264/40.6; 264/535
(58) Field of Classification Search .................. 264/410, 264/40.6, 523, 535, 537
See application file for complete search history.

(56) References Cited

U.S. PATENT DOCUMENTS

| 4,693,375 A * | 9/1987 | Schweers ...................... 209/544 |
| 6,863,860 B1 * | 3/2005 | Birckbichler et al. ........ 264/410 |
| 2004/0235970 A1 * | 11/2004 | Smith et al. .................. 521/46.5 |

FOREIGN PATENT DOCUMENTS

| EP | 2011617 A1 | 1/2009 |
| WO | WO-03002922 A1 | 1/2003 |
| WO | WO-2004066078 A2 | 8/2004 |
| WO | WO-2004104080 A1 | 12/2004 |
| WO | WO-2005095516 A1 | 10/2005 |
| WO | WO-2006060690 A2 | 6/2006 |

\* cited by examiner

*Primary Examiner* — Joseph Del Sole
*Assistant Examiner* — James Sanders
(74) *Attorney, Agent, or Firm* — Marshall, Gerstein & Borun LLP

(57) ABSTRACT

An apparatus and a method for manufacturing plastic containers, where the plastic containers are produced from a plastic material such as recycled plastic. The plastic preforms are heated in a heating unit and expanded into plastic containers in an expansion device. An infrared absorption degree of the plastic material or of the plastic preforms produced from said plastic material is then examined at least once in the course of the production process. From this examination conclusions can be drawn with respect to the quality of the preforms and their behavior when they are being heated.

8 Claims, 3 Drawing Sheets

METHOD AND APPARATUS FOR MANUFACTURING PLASTIC CONTAINERS WITH INFRARED ABSORPTION MONITORING

The present application claims the benefit of priority of European Patent Application No. 09156679.4, filed Mar. 30, 2009, which claims priority from German Patent Application No. 102008039375.4, filed Aug. 22, 2008, which claims priority from German Patent Application No. 102008019176.0, filed Apr. 17, 2008, including as to all subject matter commonly disclosed between this present application and any of the above-mentioned applications.

FIELD OF THE DISCLOSURE

The present disclosure relates to an apparatus and a method for manufacturing plastic containers, and in particular, to a method for manufacturing plastic containers from a plastic material by means of preforms, and to an apparatus for manufacturing a plurality of plastic containers from a plastic material by means of preforms.

BACKGROUND

Such apparatuses and methods are known from the prior art. The process begins with the production of plastic preforms by means of an injection molding machine. These plastic preforms normally comprise a body as well as a thread provided on said body. This thread is normally already provided in its final shape, whereas the body is expanded, by means of an expansion process, into the plastic container to be produced. It is common practice that the plastic preforms are heated by means of a heating unit prior to the actual expansion process.

More recently, it has become more and more common practice to produce the plastic material, which is used for forming the preforms, from recycled material, or to use recycled material. The use of recycled resins entails the problem that, due to batch variations, stretch-blow molding manufacturing processes necessitate greater efforts to operate the machines in question. In other words, the plastic material used for producing the preforms is not precisely uniform and, consequently, the plastic preforms produced from said plastic material are not precisely uniform either. Such batch variations originate from the different raw materials which are used in recycling processes and which are also beyond the sphere of influence of the producer of the recyclate.

These different mixtures lead to different and thus also varying heat absorption characteristics of the preforms.

These variations lead, in turn, to variations of the preform temperature achieved on the heating path of the blow molding machine, i.e., in the final analysis, an intervention on the part of the operators will be necessary more frequently; these operators have to very well trained. It may also happen that whole batches are lost, since they are not shaped in a sufficiently uniform manner, e.g. because they were not sufficiently heated.

SUMMARY OF THE DISCLOSURE

It is therefore an aspect of the present disclosure to recognize such non-uniformities and to respond to them, if necessary.

According to the present disclosure, this aspect is achieved in that the infrared absorption degree is determined in at least one area of the plastic material and that, subsequently, a value which is characteristic of this infrared absorption degree is used for producing the containers.

This aspect is also achieved in that an apparatus of the type in question includes an infrared absorption examination unit by means of which an infrared absorption degree of at least one part of the plastic material can be determined.

It will be of advantage when the preforms are produced in an injection molding or melt compression process, since a robust plastic container can then be accomplished at a reasonable price by making use of known process substeps and known devices.

It will be advantageous when the infrared absorption degree is determined at the preforms made from said plastic material. On the one hand, a characteristic value can thus already be determined very early in the production process and can be utilized during the subsequent process for a long period of time and, on the other hand, the characteristic value can be utilized at the finished preform so that, during subsequent heating and/or expansion, the respective process taking place can be influenced.

When the preforms are heated by means of a heating unit and when the heated preforms are expanded into plastic containers, known materials can be used, especially polyethylene terephthalate (PET).

It proved to be advantageous when the infrared absorption degree is ascertained during or prior to the expansion step so that the creation of the plastic container can be influenced in good time.

In order to optimally prepare already the preform for the processing following later on, it will be of advantage when the characteristic value influences, especially controls in a closed loop or in an open loop, a supply of infrared absorption material, such as carbon black, to the preforms.

It will also be advantageous when the characteristic value influences, especially controls in a closed loop or in an open loop, a heating of the preforms, since a preform can then be adapted in dependence upon its infrared absorption degree determined through the respective material and can be processed in the best possible way.

In order to minimize the reject rate of inferior-quality plastic containers, it will be of advantage when the characteristic value after the production of the preforms causes sorting of the preforms into a group of preforms having a similar infrared absorption degree or has the effect that at least one preform is sorted out.

In order to be able to process each preform independently of the previously processed or subsequently processed preform, it will be of advantage when the characteristic value controls in a closed loop or in an open loop the individual heating of each preform.

In addition, it will be advantageous when the characteristic value ascertained is compared with a stored value for influencing the process, since known material characteristics can thus be taken into account in dependence upon the infrared absorption degree ascertained.

It proved to be advantageous for an apparatus when the infrared absorption degree of a preform can be determined by the infrared absorption examination unit by making use of transmitted light and/or by working in a spatially resolved manner. On the one hand, exact information on the infrared absorption degree can be provided and, on the other hand, more reliable information on the quality of the plastic material can be provided by determining the infrared absorption degree at different locations of the plastic material.

It also proved to be advantageous when the infrared absorption examination unit is implemented for emitting light in wavelength ranges of 800 nm to 1200 nm and 1200 nm to 1500 nm and/or 2000 nm to 3000 nm and 3000 nm to 7000 nm, in particular for emitting infrared light. This allows a determination of the infrared absorption degree with the aid of simple devices and it also allows a determination of the so-called "water content" by utilizing light in the wavelength range of 2000 to 7000 nm.

For a process taking place on the apparatus, it proved to be advantageous when said apparatus comprises a heating unit and an expansion device which is arranged downstream of said heating unit and which is used for producing the plastic containers from said preforms.

In order to be able to take into account the different infrared light absorbing characteristics of the material of each individual preform, it will be advantageous when the heating unit comprises heating means which are adapted to be individually influenced with respect to their heating power by the infrared absorption degree ascertained, said heating means being in particular controllable heating means.

The method of manufacturing plastic containers according to the present disclosure is used for producing plastic preforms from a plastic material by an injection molding process or a melt compression process. According to the present disclosure, an infrared absorption degree of at least one area of the plastic material is determined, and at least one value which is characteristic of this infrared absorption degree of the plastic material is outputted.

As has already been mentioned hereinbefore, the varying plastic materials also lead to a varying heat absorption in a PET preform. This varying heat absorption, in turn, originates from varying infrared (IR) absorption characteristics. The reason for this is that the raw material producers used different percentages of infrared absorber material. The present disclosure allows to examine the infrared absorption degree and the infrared absorption characteristics so as to influence in this way the production of the plastic container and also of the plastic preforms. In this respect, the infrared absorption degree of at least one plastic preform is preferably determined after the production of said preform.

Reference should be made to the fact that the infrared absorption characteristics can be measured in a non-destructive manner. To this end, an absorption spectrometer is preferably used, which, in principle, emits infrared light that passes through a PET sample, and which evaluates the incoming infrared spectrum.

According to a preferred embodiment, the plastic material has added thereto infrared absorption material when the plastic preforms are being produced. This means that, during the production process, the plastic material has added thereto a material which is particularly suitable for absorbing infrared radiation, i.e. thermal radiation. This material can e.g. be carbon black particles or the like. Preferably, the amount of absorption material added is influenced in dependence upon the value that is characteristic of the infrared absorption degree.

It is, for example, possible that, in response to a measurement signal which indicates an insufficient infrared absorption value, the amount of infrared absorption material added is increased. This increase in the amount of absorption material added has, in turn, the effect that the absorption coefficient of the containers will be increased, whereby the heating of said containers by thermal radiation will be improved. It will be advantageous to control a pump, which supplies the infrared absorption material to the plastic material, in dependence upon the measured infrared absorption degree.

According to a preferred embodiment, the above-mentioned measurement is already used when the preforms are being produced and, consequently, a presorting of various absorption goods can be executed. It would e.g. be possible to allocate, later on, different kinds of preforms to the blow molding process, these different kinds of preforms being then heated in different ways so as to compensate the different infrared absorption characteristics in this way. If an identical absorption class is respectively used, the above-mentioned variations can be minimized in this way.

It is e.g. possible to incorporate into a post-cooling station of an injection molding machine a device for measuring the infrared absorption degree. This measurement device determines, e.g. on the basis of one preform per batch and/or shot, the infrared absorption and compares said infrared absorption with a stored database. This comparison serves to determine the infrared absorption class of the preform examined. The whole shot and/or the whole batch is conducted via a track switch into a box or receptacle corresponding to an absorption class. The plastic preforms, which are here preferably produced, are thus allocated to different groups of plastic preforms in dependence upon the measured infrared absorption degree, i.e. they are sorted.

The influence on the amount of absorption material added during the injection molding process can be derived from an online infrared absorption measurement through feedback.

The present disclosure is additionally directed to a method of manufacturing plastic containers, said method comprising the steps of heating the plastic preforms with the aid of a heating unit, through which they are preferably passed, and expanding the heated plastic preforms then into plastic containers. According to the present disclosure, an infrared absorption degree of at least one area of the plastic preforms is determined, and at least one value which is characteristic of this infrared absorption degree is outputted for the material.

It follows that also this course of action according to the present disclosure comprises determining an infrared absorption degree, but said infrared absorption degree is here determined in the method steps in which the preform is expanded into a plastic container. It should here be pointed out that the production of the plastic preforms and the forming of the plastic containers from said plastic preforms are normally not carried out by the same machines, but are in some cases executed in completely different time segments and even at different locations.

According to a preferred embodiment, the infrared absorption degree is determined with the aid of a transmitted light process. This process is particularly suitable, since it does not destroy the preform to be examined. For determining the infrared absorption characteristics, the transmission of the container for infrared radiation irradiated onto the container is preferably determined.

According to another preferred embodiment, the infrared radiation passing through the containers may also be determined in a spatially resolved manner, so as to be able to provide information on a uniformity of the material distribution.

In the case of this method according to the present disclosure, the measurement is thus preferably carried out prior to a blow molding machine, and, according to a specially preferred embodiment, the preforms are transferred into a heating path or an oven.

According to a preferred embodiment, light in a wavelength range between 800 nm and 1500 nm is used for determining the infrared absorption degree. Making use of light in this wavelength range, the infrared absorption characteristics can be examined in a particularly advantageous manner. In so doing, it is possible to provide a radiation emitting unit which emits light e.g. in a wavelength range of 1200 nm for measuring the infrared absorption degree in this way. It would, however, also be possible to cover a wavelength spectrum ranging e.g. from 800 nm to 1500 nm for judging the absorption degree.

According to another advantageous embodiment, values which are characteristic of the infrared absorption degree are compared with values stored in a memory means. In this way it can be examined, on the basis of said comparison, whether a measured absorption degree deviates from a target value so that the process can then be influenced accordingly, e.g. for removing the container in question from the production process.

According to a preferred embodiment, the plastic preforms are heated and subsequently expanded into plastic containers, and the infrared absorption degree is determined before the plastic preforms are heated.

It will be advantageous to sort out plastic preforms in dependence upon a specific absorption degree. If the infrared absorption measurements should e.g. arrive at the result that the absorption degree of the preforms is insufficient, the preforms in question can already be sorted out prior to the actual heating process and e.g. be allocated to a different kind of preforms. Unnecessary power losses or a loss of preforms in the production process can be avoided in this way.

In the case of this variant, preferably each individual preform is examined with respect to its absorption characteristics. When the method described hereinbefore is used, it will suffice to examine one preform from a batch and/or shot so as to be able to provide information on the whole shot, since it can normally be assumed that the material composition within one shot will be approximately constant. It would, however, also be possible to examine a plurality of containers from one shot so as to obtain, on the basis of suitable statistical measures, more precise information on the material composition of the shot in question.

According to another advantageous method, the water content of the preforms is determined by means of an infrared absorption measurement. This allows an additional measurement of the water content in the preform by additionally analyzing the "water spectrum", i.e. the absorption of the preform. The water content is an important core magnitude for the processing of PET and it necessitates great effort to determine it by conventional methods. It would e.g. be possible to provide an additional radiation emitting device which emits radiation in the absorption range that is characteristic of water, e.g. in a wavelength range between 2000 nm and 7000 nm, and preferably in a range between 2000 nm and 3000 nm. This measurement of the water content could simply be integrated in the above-mentioned infrared absorption measurement by providing an additional radiation emitting device which emits radiation in the water absorption range.

According to a preferred embodiment, the methods according to the present disclosure can comprise a step for heating the plastic preforms, the outputted characteristic value being used for controlling the heating step. The characteristics which have been determined with respect to the infrared absorption capacity of the plastic material and/or of the plastic preforms can thus be taken into account directly during the heating step prior to the expansion. Variations in the material composition can effectively be taken into consideration in this way. It is imaginable that the heating step is individually adapted to each individual preform which has been measured, or that the heating step is adapted to a respective class of preforms. Furthermore, this method allows a determination of the characteristic value at the blow molding machine itself or in a separate device.

It will be advantageous when, for heating the plastic preforms, each of said plastic preforms has associated therewith a heating means of its own, in particular a microwave and/or infrared heating, so as to effect individual heating. Whereas in known blow molding machines the preforms pass through a heating chamber, the provision of individual heating means allows an adaptation of the heating power of the respective heating means to the characteristic value of the preform contained therein.

In the case of this embodiment it may be advantageous when the determination of the characteristic value takes place directly before the preform enters the heating unit, so as to allow an unequivocal correlation between the respective preform and the absorption characteristics. According to one alternative it is, however, also possible to identify the preforms before they enter the heating unit, e.g. via a barcode or an RFID chip, and to compare the values in question with characteristic values stored in a database.

The present disclosure is additionally directed to an apparatus for manufacturing plastic containers, comprising an injection molding device which produces plastic preforms from a plastic material. According to the present disclosure, the apparatus comprises an infrared absorption examination unit which determines an infrared absorption degree of at least one part of the plastic material. Hence, also the apparatus according to the present disclosure provides a possibility of identifying preforms which deviate from target values in a disadvantageous manner.

According to a preferred embodiment, the absorption examination unit is arranged downstream of the injection molding device and determines an infrared absorption degree of at least one part of the plastic preform produced. Hence, also this embodiment makes it possible that specific preforms are sorted out or allocated to different classes.

According to another preferred embodiment, the absorption examination unit includes a radiation emitting device which irradiates light in an infrared wavelength range onto the plastic containers. This course of action allows a non-destructive examination of the infrared absorption degree. An advantageous embodiment may also be so conceived that a plurality of radiation emitting devices is provided, said radiation emitting devices irradiating light in infrared wavelength ranges onto the plastic containers. The preform can be examined at several locations in this way so that the infrared absorption degree can also be evaluated statistically and so as to exclude that an area having a particularly high infrared absorption degree may corrupt the measurement.

According to another preferred embodiment, the absorption examination unit includes a radiation detector device which detects light that has been irradiated onto and transmitted by the plastic containers. In principle, a measurement could be carried out by means of a spectroscope, but spectroscopes are comparatively expensive.

Hence, it is e.g. possible to use two or three diodes as radiation emitting devices, said two or three diodes having a defined spectrum, as well as a receiver that is suitable for the range in question. It is thus possible to avoid the problem of the so-called lamp ageing of conventional spectrometers. In addition, the solution in the case of which only two or three diodes are provided is less expensive and less time-consuming. Such infrared diodes do essentially not age and, consequently, they have a long service life and they emit a clearly defined narrow spectrum range.

The radiation detector device is preferably arranged such that, with respect to the preforms to be examined, it is disposed in opposed relationship with the radiation emitting device, so as to detect and analyze the light transmitted by the preform.

In addition, the absorption examination unit preferably comprises an additional radiation emitting device, which emits radiation in a wavelength range between 2000 nm and 3000 nm. This additional radiation emitting device is especially used for examining water inclusions in and/or a water content of the preforms produced. According to a preferred embodiment, also a plurality of such additional radiation emitting devices is provided, which examine the water content in several areas of the preform. Also this course of action allows an avoidance of measurement errors caused by local water content maxima.

The present disclosure is additionally directed to an apparatus for manufacturing plastic containers, said apparatus comprising a heating unit which heats plastic preforms, and an expansion device following said heating unit and used for expanding the heated plastic preforms into plastic containers. According to the present disclosure, said apparatus comprises an absorption examination unit which determines an infrared absorption degree of at least one part of the plastic preform. The apparatus is preferably implemented in the way described hereinbefore. The absorption examination unit is preferably arranged upstream of the heating unit. In accordance with a further advantageous embodiment, a transport unit is provided, which transports the containers though the heating unit or moves them past heating elements.

The present disclosure additionally relates to an apparatus for manufacturing plastic containers, in particular an apparatus of the type described hereinbefore, comprising a heating unit which heats plastic preforms as well as an expansion device which follows said heating unit and which expands the heated plastic preforms into plastic containers. This apparatus is characterized by a unit for controlling the heating unit, which is implemented such that, for controlling the heating of the plastic preforms, a value that is characteristic of the infrared absorption degree of the individual plastic preforms is used. It follows that the infrared absorption capacity of the material can be taken into account in the open loop and/or closed loop control process of the heating-unit. The value used for the open loop control process is preferably the characteristic value that has been determined for each individual preform. It is, however, also possible to use an e.g. averaged value that has been determined for a group.

According to a preferred embodiment, the heating unit can comprise a plurality of individually controllable heating means, in particular microwave and/or infrared heatings, whose heating power can be adjusted individually. This makes it possible it to take into account material variations so as to reduce variations in the end product. Individual heating means have the advantage that, due to their small volume, they can rapidly be adapted to changed parameters. The preforms are here no longer passed through a common heating unit, but the individual heating means can be implemented such that they move together with the preforms in the blow molding machine.

The control unit can advantageously be implemented such that the heating power of a heating means can be controlled on the basis of the characteristic value of the preform contained in the respective heating means. Varying material compositions can thus be taken into account from one preform to the next.

BRIEF DESCRIPTION OF THE DRAWINGS

Further advantages and embodiments can be seen from the drawings enclosed, in which.

DETAILED DESCRIPTION OF THE PREFERRED EMBODIMENT

Figure 1:
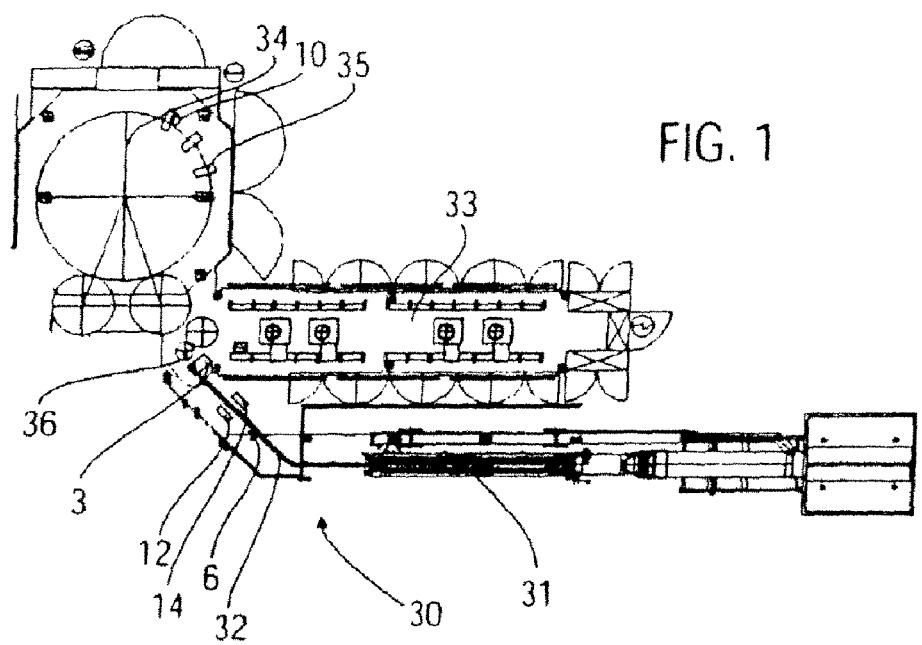
FIG. 1 shows an apparatus for manufacturing plastic containers according to the present disclosure.

FIG. 1 shows a container manufacturing apparatus 30 according to the present disclosure. Said apparatus 30 comprises a sorting device 31 which imparts a specific orientation to the incoming preforms 10. Subsequently, these preforms 10 are supplied to a transport unit 32, such as a chute, along which they are conducted to a metering star wheel 36. This metering star wheel 36 is followed by a heating unit 33 through which the containers are passed so as to be subsequently expanded into plastic containers in a blow molding unit 34.

This blow molding unit 34 has a plurality of processing stations 35 in which the preforms 10 are expanded into containers. Upstream of the heating unit 33, an infrared absorption examination unit is provided, which is designated generally by reference numeral 6.

The present embodiment of this infrared absorption examination unit 6 comprises a large number of radiation emitting devices 11, 12, 13 which emit radiation that passes through the containers 10 and falls onto sensor devices or radiation detector devices 14, 16, 18. These sensor devices 14, 16, 18 measure the radiation that passed through the containers and determine in this way an absorption degree of the individual containers. Reference numeral 3 refers to an ejection device by means of which individual containers can be removed from the apparatus, e.g. containers having an insufficient infrared absorption coefficient.

It would also be possible to arrange the ejection device 3 downstream of the heating unit 33. In this case, the ejection device 3 may be coupled to the infrared absorption unit so as to allow an effective ejection of containers whose infrared absorption degree is insufficient.

Figure 2:
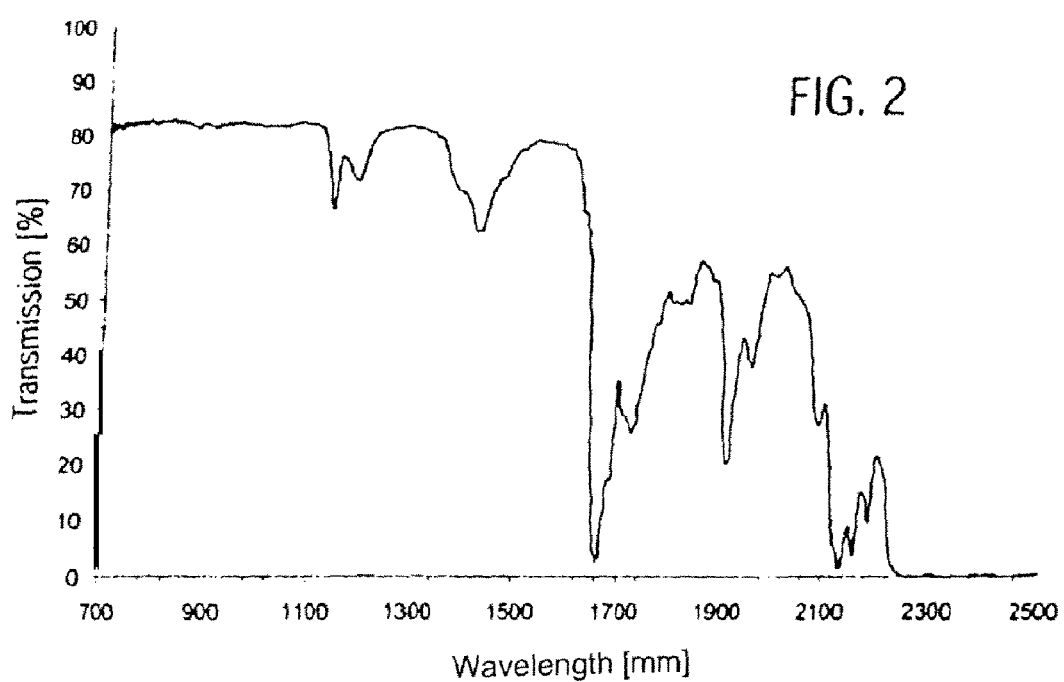
FIG. 2 shows a recorded infrared absorption spectrum of a container.

FIG. 2 shows an example for a recorded infrared absorption spectrum of an examined container. It can here be seen that, in a wavelength range between 700 and 1500 nm, a high percentage of the infrared power is transmitted. It would e.g. be possible to store the spectrum, which is shown in FIG. 2, as a reference and to compare it with recorded infrared absorption data. If e.g. certain containers should have a substantially higher transmission, it can, vice versa, be concluded that their infrared absorption is low. These containers could then be allocated to a different class of containers.

As has been explained hereinbefore, it is thus possible to form different classes or groups of containers; for manufacturing the plastic containers, the heating unit 33 could then be adapted to these different classes in each individual case, and different classes of containers could be treated differently and/or heated to different temperatures. It would also be possible to adapt the parameters of the expansion device 34 to the different classes of containers.

Figure 3:
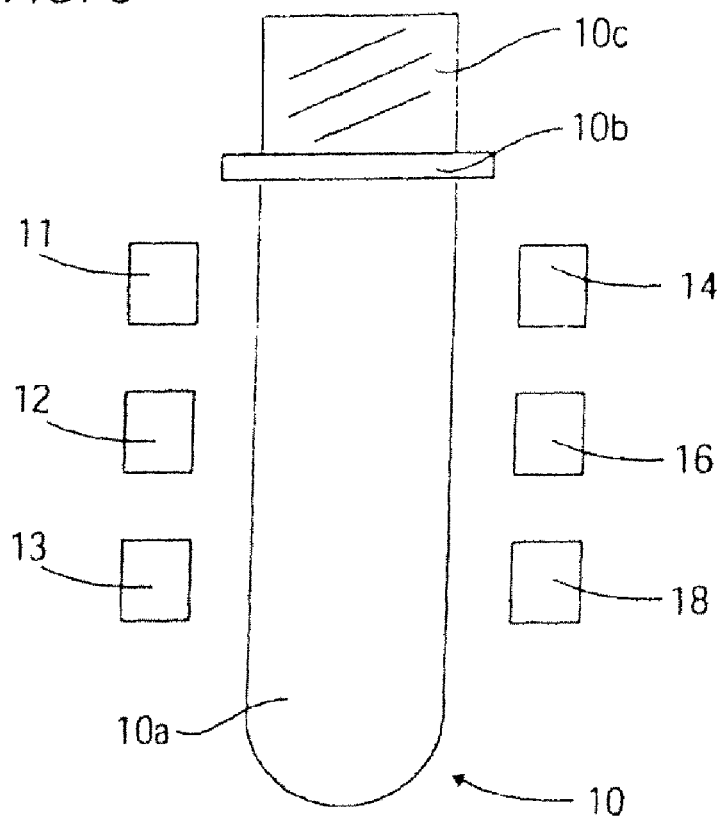
FIG. 3 shows a representation illustrating the arrangement of an infrared absorption examination unit.

FIG. 3 shows a schematic representation for illustrating an infrared absorption measurement. Three radiation emitting devices 11, 12, 13, which are disposed one above the other, are here shown, each of said devices irradiating infrared light onto a container 10 or, more precisely, onto a body 10a of said container 10. This light is, at least partially, transmitted by the container and falls onto radiation detector devices 14, 16, 18. The sensor wavelengths are adapted to the wavelengths of the radiation emitting devices 11, 12, 13. The area above a supporting ring 10*b*, i.e. the area on the level of a thread 10*c*, is preferably not provided with any infrared absorption examination units, since an expansion of the containers 10 does not take place in this area.

The three radiation emitting devices 11, 12, 13 may emit different wavelength ranges, e.g. the upper radiation emitting device a wavelength in the range of 800 nm, the central radiation emitting device a wavelength in the range of 1200 nm, and the third radiation emitting device a wavelength in the range of 2500 nm. Said third radiation emitting device 13 is therefore particularly suitable for detecting a water content within the preform 10. The wavelengths of the third radiation emitting device may, however, also be much higher, e.g. in a range between 6000 nm and 7000 nm, for examining the presence of water.

Figure 4:
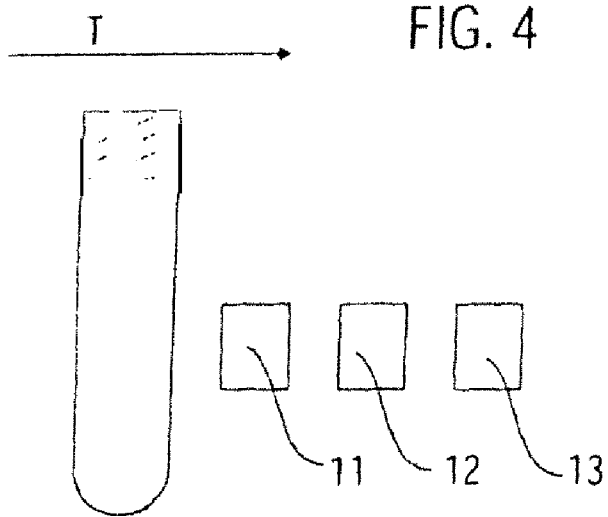
FIG. 4 shows another representation illustrating the arrangement of an infrared absorption examination unit.

FIG. 4 shows another embodiment of an absorption unit according to the present disclosure. The container, which is generally designated by reference numeral 10, is here moved past three radiation emitting devices 11, 12, 13 in the direction of transport. These three radiation emitting devices 11, 12, 13 are arranged in front of the container in FIG. 4, whereas the radiation detector devices 14, 16, 18, which are associated with the individual radiation emitting devices 11, 12, 13 and which have already been described in connection with FIG. 3, are arranged behind the container. A continuous radiation detector device may, however, be used as well. Instead of the arrangement shown in FIG. 4, it would also be possible to provide a spectrometer for the purpose of examining the infrared absorption.

Figure 5:
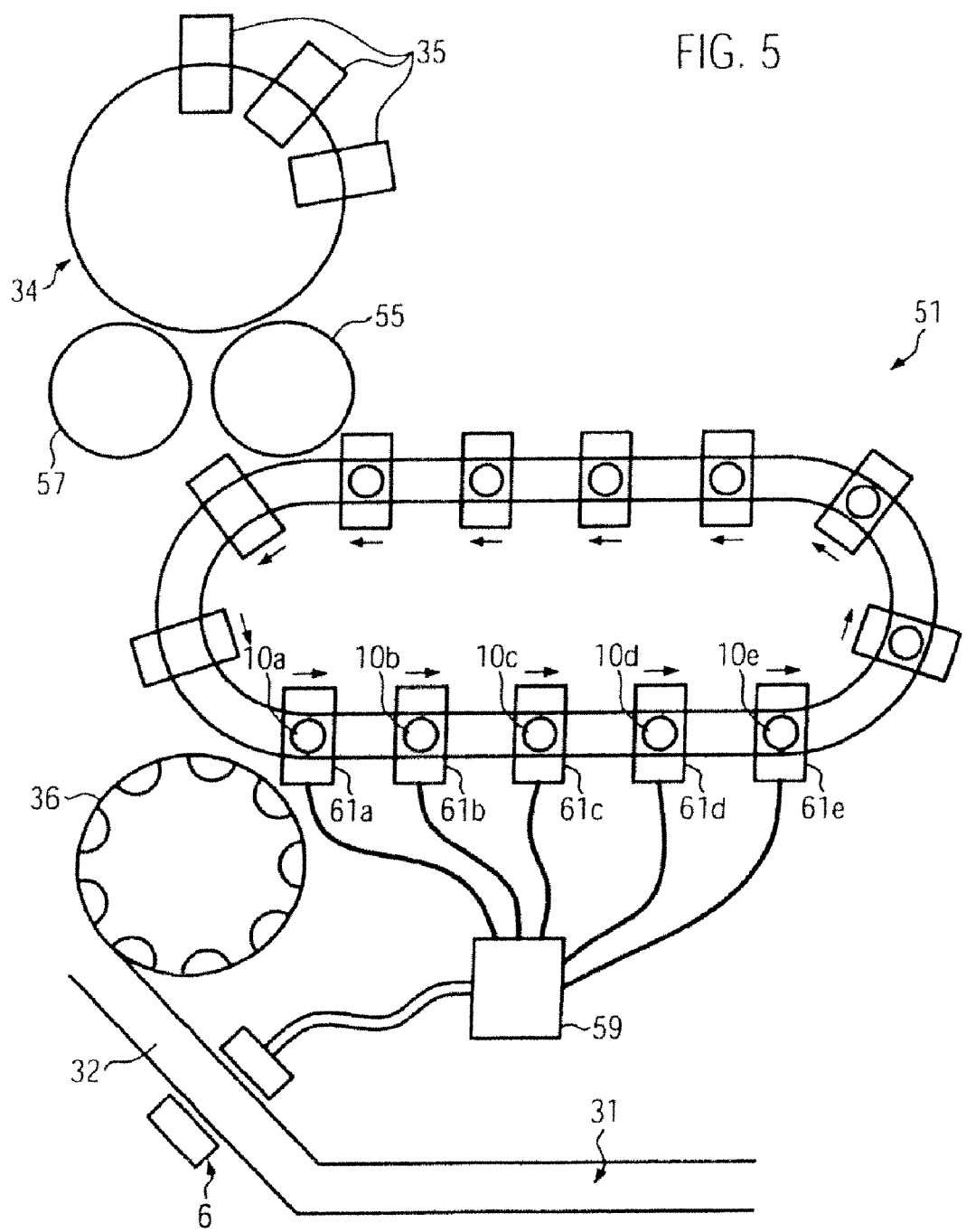
FIG. 5 shows a further embodiment of an apparatus for manufacturing plastic containers according to the present disclosure.

FIG. 5 shows another embodiment of a container manufacturing apparatus 51 according to the present disclosure. Elements and features of said apparatus provided with reference numerals corresponding to those used in FIG. 1 to 4 will not be described in detail once more. They will be described by making reference to the preceding text.

The apparatus 51 comprises a sorting device 31 for orienting the preforms 10, and a transport unit 32 through which the preforms 10 are transferred to a metering star wheel 36. Following this, the preforms pass through a heating unit which is modified in comparison with the unit shown in FIG. 1. This heating unit is followed by the blow molding unit 34 with its feeder star wheel 55 and the processing stations 35, where the preforms 10 are expanded into containers and then discharged via a delivery star wheel 57.

Just as in the case of the apparatus according to FIG. 1, an infrared absorption examination unit 6 is provided upstream of the heating unit; said infrared absorption examination unit has already been described in detail in connection with FIG. 2 to 4. This unit 6 provides characteristic values for the infrared absorption degree of the plastic preforms 10 moving past said unit.

In this embodiment, these values are transmitted to a control unit 59. This control unit may also be a closed loop control unit, depending on how the characteristic values are used. The control unit 59 makes use of the determined characteristic values for controlling the heating unit in accordance with the preform absorption characteristics ascertained. This allows a direct response to changes in the properties of the material in question.

The heating unit of this embodiment comprises a plurality of individual heating means 61*a*-61*e*. These heating means are implemented such that each of them can receive therein a preform 10*a*-10*e* and heat said preform individually. The preforms 10, 10*a*-10*e* are then heated to the desired temperature before they are transferred to the blow molding unit 34 which is implemented as a processing station. It follows that the individual heating means 61*a*-61*e* move together with the preforms (indicated by the arrows in FIG. 5). Individual heating means 61*a*-61*e* have the advantage that, due to their small volume, they can be adapted to modified parameters within a short period of time.

The individual heating means 61*a*-61*e* communicate with the control unit 59 (shown only for 61*a*-61*e*, but provided for all the heating means). Hence, the control unit 59 is able to control the heating means 61*a*-61*e* for each preform 10*a*-10*e* individually in dependence upon the characteristic values that have been ascertained with respect to the infrared absorption. The infrared absorption capacity of the respective material can thus be taken into account when the heating means are controlled in an open loop or in a closed loop.

Alternatively to the use of the individual characteristic values, it is, however, also possible to use an e.g. averaged value that has been ascertained for a group.

The individual heating means 61*a*-61*e* are preferably implemented as microwave or infrared heatings. These kinds of heatings respond sufficiently fast to changes of parameters.

Just as in the case of FIG. 1, also this embodiment may, of course, comprise an ejection device by means of which individual, in particular faulty preforms can be removed from the manufacturing process.

In FIG. 5, the examination unit 6 is a part of the apparatus itself. It is, of course, also imaginable to determine the characteristic values of the infrared absorption in a separate, independent device. In this case, it would be necessary to execute in the apparatus 51 an identification of the preforms through which a preform can unequivocally have associated therewith the respective characteristic value belonging thereto. This can be done e.g. by means of printed-on barcodes or RFID chips. The values in question can then be taken from a database.

Summarizing, it can therefore be stated that, in the apparatus 51, the heating power can be adapted individually to varying material properties from one preform to the next. This will improve the machine throughput.

Making use of the apparatus 51, containers are produced as follows: via the sorting device 31 and the transport unit 32, the preforms are moved past the examination unit 6 one after the other. At the examination unit 6, at least one value which is characteristic of the infrared absorption is determined for each preform 10, 10*a*-10*e*, said value/values being then transmitted to the control unit 59.

Following this, the preforms 10, 10*a*-10*e* pass through the heating unit; in the course of this process, each preform is heated, e.g. through microwave or infrared radiation, in a separate heating means 61*a*-61*e* moving together with the respective preform. The heating of the individual heating means is controlled in an open loop or in a closed loop by the control unit 59. In so doing, the characteristic value ascertained is taken into account. It follows that each preform is heated in a manner adapted to the infrared absorption behavior of the respective preform, and this means that material compositions varying e.g. due to the recycling mixture used can be taken into account.

Subsequently, the heated preforms are expanded into the final plastic containers in the blow molding unit 34 and can be transported away via the delivery star wheel 57.

In the following, various embodiments are described.

A method of manufacturing plastic containers comprises producing plastic preforms from a plastic material by an injection molding process, where an infrared absorption degree of at least one area of the plastic material is determined, and where at least one value which is characteristic of this infrared absorption degree of the plastic material is outputted.

A method as above where the infrared absorption degree of at least one plastic preform is determined after the production of the preform.

A method as one of the above embodiments, and when the plastic preforms are being produced, the plastic material has added thereto an infrared absorption material, and where the amount of the infrared absorption material added is preferably influenced in dependence upon the value that is characteristic of the infrared absorption degree.

A method as one of the above embodiments, and where the plastic preforms produced are allocated to different groups of plastic preforms in dependence upon the measured infrared absorption degree.

A method of manufacturing plastic containers, including heating plastic preforms with the aid of a heating unit, and expanding the heated plastic preforms then into plastic containers, and where an infrared absorption degree of at least one area of the plastic preforms is determined, and where at least one value which is characteristic of this infrared absorption degree is outputted for the plastic preform and/or that the infrared absorption degree is determined with the aid of a transmitted light process, and wherein the light used is especially light in a wavelength range between 800 nm and 1500 nm and/or wherein values which are characteristic of the infrared absorption degree are compared with values stored in memory.

A method as one of the above embodiments, and where the plastic preforms are heated and subsequently expanded into plastic containers, and where the infrared absorption degree is determined before the plastic preforms are heated.

A method as one of the above embodiments, and where the plastic preforms are sorted out in dependence upon the absorption that is degree determined.

A method as one of the above embodiments, where, by way of an infrared absorption measurement, a water content of the preforms is determined and/or where heating the plastic preforms is provided, and where the outputted characteristic value is used for controlling the heating step and where, for heating the plastic preforms, each of the plastic preforms has preferably associated with it a heating unit of its own, and in particular by a microwave and/or infrared heating unit, so as to effect individual heating.

Then, there is an apparatus for manufacturing plastic containers, including an injection molding device which produces plastic preforms from a plastic material, and where the apparatus includes an absorption examination unit (6) which determines an infrared absorption degree of at least one part of the plastic material, and where, preferably, the absorption examination unit (6) is arranged downstream of the injection molding device and determines an infrared absorption degree of at least one part of the plastic preforms (10) that are produced.

An apparatus as above, and where the absorption examination unit (6) includes a radiation emitting device (11, 12) which irradiates light in an infrared wavelength range onto the plastic containers, and where, preferably, the absorption examination unit (6) includes a radiation detector device (14, 16, 18) which detects light that has been irradiated onto and transmitted by the plastic containers (10).

An apparatus as one of the above embodiments, and where the absorption examination unit (6) includes an additional radiation emitting device (13) which emits radiation in a wavelength range between 2000 nm and 7000 nm.

An apparatus (30) for manufacturing plastic containers, that includes a heating unit (33) which heats plastic preforms and an expansion device (34) following said heating unit (33) and which expands the heated plastic preforms (10) into plastic containers, and where the apparatus (30) also includes an absorption examination unit (6) which determines an infrared absorption degree of at least one part of the plastic preform (10).

An apparatus (30) as above, and where the absorption examination unit (6) is implemented with at least one of the preceding embodiments.

An apparatus (30) for manufacturing plastic containers, as one of the above embodiments, and including a heating unit which heats plastic preforms as well as an expansion device (34) following the heating unit and expanding the heated plastic preforms (10) into plastic containers, and including a unit (59) used for controlling the heating unit and implemented such that, for controlling the heating of the plastic preforms, a value is used which is characteristic of the infrared absorption degree of the individual plastic preforms, with the heating unit being preferably a plurality of individually controllable heating units (61a, 61b, 61c, 61d, 61e), and in particular a microwave and/or infrared heating units, whose heating power can be adjusted individually.

An apparatus as above and where the control unit (59) is implemented such that the heating power of a heating means (61a, 61b, 61c, 61d, 61e) is adapted to be controlled on the basis of the characteristic value of the respective preform contained in the heating means in question.

The invention claimed is:

1. A method of manufacturing plastic containers from a plastic material using preforms, comprising:
   determining an infrared absorption degree in at least one area of the plastic material and, subsequently, using a value which is characteristic of the infrared absorption degree for producing the containers;
   heating the preforms by means of a heating unit and expanding the heated preforms into plastic containers;
   determining the infrared absorption degree one of during or prior to the expansion step; and
   influencing by the characteristic value a supply of infrared absorption material to the preforms, and the characteristic value influence causes control of the supply in a closed loop.

2. A method according to claim 1, and determining the infrared absorption degree at the preforms made from the plastic material.

3. A method according to claim 1, and producing the preforms in one of an injection molding process or a melt compression process.

4. A method according to claim 1, wherein the characteristic value influences a heating of the preforms.

5. A method according to claim 1, wherein the characteristic value after the production of the preforms causes one of sorting of the preforms into a group of preforms having a similar infrared absorption degree or has an effect that at least one preform is sorted out.

6. A method according to claim 1, wherein the characteristic value controls in one of a closed loop or an open loop the individual heating of each preform.

7. A method according to claim 1, wherein the characteristic value is compared with a stored value for influencing the process of producing the containers.

8. A method according to claim 4, and wherein the characteristic value influence causes control of the heating in one of a closed loop and an open loop.

* * * * *